United States Patent [19]

Melville

[11] Patent Number: 4,511,495

[45] Date of Patent: Apr. 16, 1985

[54] TUMBLE DRYER PRODUCTS FOR DEPOSITING PERFUME

[75] Inventor: James B. Melville, Wirral, England

[73] Assignee: Lever Brothers Company, New York, N.Y.

[21] Appl. No.: 258,253

[22] Filed: Apr. 28, 1981

[30] Foreign Application Priority Data

May 16, 1980 [GB] United Kingdom ................. 8016244

[51] Int. Cl.$^3$ .......................... A61K 7/46; B05D 3/12

[52] U.S. Cl. .................................... 252/522 A; 34/9; 252/8.8; 427/242; 428/279; 428/305.5; 428/905

[58] Field of Search ............ 427/242; 252/8.8, 522 A; 428/905, 305.5, 279; 34/9, 12

[56] References Cited

U.S. PATENT DOCUMENTS

| | | | |
|---|---|---|---|
| 3,442,692 | 5/1969 | Gaiser | 427/242 X |
| 4,012,326 | 3/1977 | Rudy | 252/8.8 |
| 4,134,838 | 1/1979 | Hooper et al. | 252/8.6 X |
| 4,152,272 | 5/1979 | Young | 252/8.8 |

FOREIGN PATENT DOCUMENTS 1544863 4/1979 United Kingdom .

*Primary Examiner*—Evan K. Lawrence
*Attorney, Agent, or Firm*—Milton L. Honig; James J. Farrell

[57] ABSTRACT

Perfume may be deposited on fabrics by drying wet fabrics in a rotary hot air dryer together with a conditioning composition containing (i) a fabric conditioning agent such as a fabric softener and (ii) particles containing an intimate mixture of a perfume and an amine, particularly a primary or tertiary amine, having an alkyl substituent with from 1 to 22 carbon atoms. The particles may also contain nonionic materials. The conditioning composition may be coated on a substrate, suspended in a liquid medium for spraying onto the fabrics or onto the surfaces of the dryer, or may be in the form of a paste for applying to some of the fabrics before drying. Alternatively the composition may be in particulate form for sprinkling onto the fabrics. The method leads to efficient use of the perfume.

6 Claims, No Drawings

TUMBLE DRYER PRODUCTS FOR DEPOSITING PERFUME

FIELD OF THE INVENTION

This invention relates to tumble dryer products capable of depositing perfumes on fabric surfaces. The products may be used in a variety of forms and examples of the fabric surfaces are cotton, wool, polyacrylic, polyamide and polyester fibres. These products are intended for use in the dryer cycle of a fabric cleaning operation.

The products of the invention will normally be used to provide a fabric conditioning (eg fabric softening) effect.

Perfumes are liquid compositions consisting of a number of organic compounds, capable of appreciation by smell. The compounds are usually derived from natural sources but synthetic materials are also used.

Formulations intended for the laundering of fabric will normally contain a perfume to provide a pleasant after smell on the laundered fabrics. Thus powder and liquid detergent formulations, rinse cycle formulations and tumble dryer products contain perfumes.

It is desirable to have the perfume in a fabric treatment formulation used efficiently because it is a relatively high cost component of any formulation.

BACKGROUND ART

The desirability of enhancing the effectiveness of perfumes has been acknowledged in the patent literature. U.S. Pat. No. 4,152,272 (Young) describes a fabric conditioning composition comprising particles of a wax-like carrier and a perfume. British Patent Specification No. 1 544 863 (Schilling et al) describes a fabric conditioning composition for use in an automatic laundry dryer comprising particles of a mixed cationic/nonionic carrier and a perfume. In German Patent Application No. 2 732 985 of Unilever Limited a deposition system is described which provides increased deposition of materials providing a perceivable effect, for example perfumes. Amines are disclosed as matrix materials, but a cationic material is required as an essential component of the dispersed phase including the perceivable component.

DISCLOSURE OF THE INVENTION

We have now discovered that surprisingly good perfume deposition on fabrics can be achieved without the incorporation of cationic materials in perfume-carrying amine particles. Thus, according to the invention, there is provided a method of depositing perfume on fabrics in a rotary hot air dryer in which a perfume containing fabric conditioning composition is placed in the dryer before, simultaneously with or after the addition of wet fabrics to the dryer and the dryer is then operated to dry on the fabrics, characterised in that said fabric conditioning composition comprises (i) a first phase constituting from about 0.5% to about 50% by weight of the composition and consisting of particles having an average size of from about 0.1 micron to about 200 microns, the particles comprising an intimate mixture of (a) from about 0.5% to about 50% by weight, based on the weight of the particles, of a perfume, and (b) from about 50% to about 99.5% by weight, based on the weight of the particles of a matrix comprising at least one water dispersible amine of the formula $$R—N\,R^1R^2$$

where R is an alkyl or alkenyl group having from 8 to 22 carbon atoms, $R^1$ is hydrogen or an alkyl or alkenyl group having 1 to 4 carbon atoms and $R^2$ is hydrogen or an alkyl, alkenyl or amino-alkyl group having from 1 to 22 carbon atoms, the matrix containing no added cationic material; and (ii) a second phase constituting from about 0.5% to about 80% by weight of the composition and comprising a fabric conditioning agent.

The two phases of the fabric conditioning composition may be dispersed in each other or in an inert solid or liquid dispersion medium. Additionally, or alternatively the fabric conditioning composition may be present together with an inert solid or liquid carrier medium.

Thus, in one embodiment of the invention the fabric conditioning composition is supported on a solid carrier such as a flexible substrate. This substrate may be constituted by a sheet of porous or non-porous material onto at least one face of which the composition is coated and/or impregnated.

Suitable sheet materials for this purpose include polyurethane foam, paper, plastics material, metal foil, and no-woven cloth.

As further alternatives for the inert carrier may be mentioned porous or non-porous balls on which the fabric conditioning composition is coated and/or impregnated and also containers adapted to be fixed inside the tumble dryer and having means for releasing the fabric conditioning composition onto the fabrics in use.

In a second embodiment of the invention, the fabric conditioning composition in particulate form is sprinkled over the fabrics in the dryer.

In a further embodiment of the invention, the fabric conditioning composition in liquid form, may be sprayed onto the inside surfaces of the dryer and/or onto the fabrics prior to operation of the dryer. To form the product into a liquid, the composition may be dispersed in a liquid carrier such as water or an aerosol propellant. Suitable such propellants include hydrocarbons and fluorocarbons. Preferably the amine/perfume particles are insoluble in the propellant. In a still further embodiment, the fabric conditioning composition in the form of a paste or cream is applied to a portion of the fabrics prior to operation of the dryer. To form the product into a paste or cream, the composition may be mixed with a liquid carrier, such as water.

The alkyl groups, alkenyl groups and alkyl portion of the amino-alkyl groups may be linear or branched. Preferably the amine is a primary or tertiary compound or a diamine, particularly a diamine of the formula $R—NH—(CH_2)_3—NH_2$, where R is as defined above. Preferred compounds are methyl dihardened tallow tertiary amine, hardened tallow primary amine, methyl, dicocotertiary amine, coco primary amine and N-alkyl 1:3 propylene diamines, where the alkyl group may be hardened tallow, coconut or $C_{18}/C_{20}$ mixture. The amines of utility in the invention can be solid, liquid or pasty and will have solubility in water of not more than about 1% weight/volume.

The fabric conditioning agent may be selected from the classes of fabric softening agents, antistatic agents, lubricating, bacteriostatic, mildew proofing or moth proofing agents, for example dialkyl quaternary ammonium salts eg distearyl dimethyl ammonium chloride;

amine salt derivatives; amphoteric compounds eg alkyl sulphobetaines and imidazoline derivatives; agents formed by complexing cationic and anionic species, eg as described in UK Pat. Specification No. 2 007 735.

A list of suitable conditioning materials is given in German Patent Application No. 2 732 985.

The perfume may be selected from any perfumes and any mixtures thereof. Examples of fabric substantive perfumes suitable for use in the present invention are listed in S Arctander, Perfume Flavors and Chemicals, Volumes I and II, published by the Author, Montclair, N.J., USA and the Merck Index, 8th Edition, Merck & Co Inc., Rahway, N.J., USA. Deodorant perfumes such as disclosed in U.S. Pat. No. 1,134,838 may also be used.

The products may include other components. In particular a distributing agent may be included to aid the uniform spreading and application of the fabric conditioning agent and the amine/perfume particles to the fabrics in the dryer. Examples of such distributing agents include urea, ammonium carbonate, nonionic compounds, and waxes. The distributing agent may also act as a second fabric conditioning agent. The distributing agent may constitute from about 5% to about 95%, preferably from about 20% to about 80% by weight of the product.

In the case where the product is in the form of a composition carried on a flexible substrate, the composition may form from about 50% to about 80% by weight of the product, preferably from about 60% to about 75% of the product. Thus the weight ratio of composition to substrate is within the range of about 1:1 to about 4:1, preferably about 1.7:1 to about 3:1. In such embodiments the composition may comprise from about 20% to about 70% by weight, preferably from about 40% to about 60% of the fabric softening agent(s) and from about 10% to about 40%, preferably from about 14% to about 30% by weight of particles, these percentages being based on the total weight of the product.

In the case where the product is in the form of a particulate mixture for sprinkling on the fabrics in the dryer, the mixture preferably comprises from about 25% to about 75% particles and from about 25% to about 75% by weight fabric softening agent(s).

When the product is in the form of a sprayable liquid, it may comprise from about 1% to about 10% by weight, preferably from about 2% to about 7% by weight particles and from about 5% to about 25%, preferably from about 10% to about 15% fabric softening agent(s), the major part of the balance being a liquid vehicle such as water and/or a propellant. Means for spraying the sprayable liquid form of the product onto the inside surfaces of the dryer and/or onto the fabrics prior to operation of the dryer may be constituted by a hand sprayer or by a pressurised aerosol spray device of known construction. The spray nozzle of such a device should have a size so related to the maximum particle size of the fabric conditioning composition that the nozzle will not become clogged thereby.

When the product is in the form of a cream or paste, the solids contents will generally be higher. Thus there may be from about 5% to about 40%, preferably from about 20% to about 25% by weight of fabric softening agents.

A method of preparing the products of the invention includes the step of forming a liquid mixture of the amine and the perfume. This mixture is then either dispersed in water, cooled and filtered or cooled and ground to the required size. The amine/perfume particles are then simply mixed with the other components of the product.

Where the product is in the form of a composition carried on a substrate, the various components of the composition may be premixed and thereafter applied to the substrate separately. Thus, in the latter case, the fabric conditioning agents may be applied to the substrate in molten form and then the particles are added thereto.

The invention will now be further illustrated by the following non-limiting Examples.

EXAMPLE 1

9.5 g of methyl di-hardened tallow amine was melted and 0.5 g of perfume added. The amine was maintained as near to its melting point as possible consistent with good mixing. The melt was then cooled and ground to give an average particle size of 50–200 microns.

0.5 g of dimethyl di-hardened tallow ammonium chloride and 2.0 g of sorbitan monostearate as a distributing agent and second fabric softening agent were mixed, melted and then coated on a 9"×11" sheet of non-woven rayon weighing 1.5 g. While the coating was still partially molten, 1.0 g of the above mentioned particles were sprinkled on so that they became embedded in the coating as it cooled. The overall composition of the product was therefore approximately:

| | |
|---|---|
| Inert carrier | 30.0% |
| Cationic fabric softening agent | 10.0% |
| Distributing agent | 40.0% |
| Particles | 20.0% |
| (Amine) | (19.0%) |
| (Perfume) | (1.0%) |

The product was then placed in a "CREDA REVERSOMAT" tumble dryer together with a 1.6 kg load of freshly washed fabrics, consisting of a mixture of terry towelling and bulked acrylic. The dryer was operated for 45 minutes. The resulting fabrics had excellent softness and good perfume substantivity.

EXAMPLE 2

1.0 g of the particles prepared as described in Example 1 were mixed with 0.5 g of dimethyl di-hardened tallow ammonium chloride which had been ground and sieved to a particle size of 50–200$\mu$ and were sprinkled onto a 7 lb load of freshly washed fabrics in a "CREDA REVERSOMAT" tumble dryer. The load consisted of a mixture of terry towelling and bulked acrylic. The dryer was operated for 45 minutes. The resulting fabrics had excellent softness and good perfume substantivity.

EXAMPLE 3

9.5 g of Cemamime P970 was melted together with 0.5 g perfume. After thorough mixing the melt was allowed to cool to a solid and ground to a particle size of 50–200 microns.

1.5 g of Arosurf TA 100, a cationic fabric softening agent, was melted together with 6.0 g sorbitan monostearate to act as a distributing agent. After thorough mixing the melt was allowed to cool to a solid and ground to a particle size of 50–200 microns.

2.5 g of the cationic/nonionic particles were then thoroughly mixed with 1 g of the carrier/perfume particles to give a solid particulate product having the following approximate overall composition:

| | |
|---|---|
| Distributing agent | 57% |
| Fabric softening agent | 14% |
| Particles | 29% |
| (Amine) | (27.5%) |
| (Perfume) | (1.5%) |

3.5 g of this mixture was sprinkled onto a fabric load in a tumble dryer drum (BURCO TUMBLAIR DRYER), the load consisting of 800 g terry toweeling (75% water content) and 800 g acrylic (50% water content). The dryer was operated for 45 minutes after which the presence of perfume on the fabrics could be positively identified.

EXAMPLE 4

100 ml of an aqueous dispersion containing 2.5% Arosurf TA 100 cationic fabric conditioning agent was heated to 50° C. and 10 g of sorbitan monostearate was added. Mixing was carried out using an ultrasonic probe. To 48 ml of this dispersion was then added 2 g of carrier/perfume particles made by the same method as described in Example 3. The liquid product so formed had the following approximate overall composition:

| | |
|---|---|
| Distributing agent | 9.6% |
| Fabric softening agent | 2.4% |
| Particles | 4.0% |
| (Amine) | (3.8%) |
| (Perfume) | (0.2%) |
| Water | balance |

25 g of this product was sprayed onto a load of fabrics in a tumble dryer drum and the dryer was operated to dry the fabrics. The composition of the load, the dryer type and the operating conditions were the same as in Example 3. After drying, the presence of perfume on the fabrics could be positively identified.

EXAMPLE 5

2.5 g Arosurf TA100, a cationic fabric softening agent, was melted together with 10 g sorbitan monostearate to act as a distributing agent and thoroughly mixed. The molten mixture was then added to 37.5 g water with stirring to form a cream or paste. 10 g of this cream had added thereto 1 g of carrier/perfume particles made in the same way as in Example 3. The product so found had the following approximate overall formulation:

| | |
|---|---|
| Distributing agent | 18.2% |
| Fabric softening agent | 4.5% |
| Particles | 9.1% |
| (Amine) | (8.65%) |
| (Perfume) | (0.45%) |
| Water | balance |

The cream was spread onto one piece of terry towelling taken from a fabric load similar to that described in the dryer drum. The dryer was then operated. The dryer type and operating conditions were the same as in Example 3. After drying, the present of perfume on the fabrics could be positively identified. Similar results were obtained where the cream was spread over the interior surface of the dryer drum before operating the dryer.

The perfume used in these Examples had the following approximate formulation:

| LF 165 | % |
|---|---|
| Benzyl Salicylate | 5.0 |
| Musk Xylene | 5.0 |
| Galaxolide 50% | 5.0 |
| Hexyl Cinnamic Aldehyde | 10.0 |
| Lilial | 5.0 |
| Hydroxycitronellal | 6.0 |
| Methyl Dihydro Jasmonate | 8.0 |
| Citronellol Standard | 5.0 |
| Geraniol Standard | 5.0 |
| Phenyl Ethyl Alcohol | 10.0 |
| Oil of Gergamot Synthetic | 5.0 |
| Oil of Geranium Bourbon | 5.0 |
| Oil of Lavandin | 5.0 |
| Trichlor Methyl Phenyl Carbinyl Acetate | 2.0 |
| Oil of Patchouli | 1.0 |
| Linalol | 10.0 |
| Coumarin | 2.0 |
| Benzyl Acetate | 2.0 |
| Terpineol | 4.0 |
| | 100.0 |

What is claimed is:

1. A method of depositing perfume on fabrics in a rotary hot air dryer in which a perfume-containing fabric conditioning composition is placed in the dryer before, simultaneously with, or after the addition of wet fabrics to the dryer and the dryer is then operated to dry the fabrics, characterised in that said fabric conditioning composition comprises (i) a first phase constituting from about 0.5% to about 50% by weight of the composition and consisting of particles having an average size of from about 0.1 micron to about 200 microns, the particles comprising an intimate mixture of (a) from about 0.5% to about 50% by weight, based on the weight of the particles, of a perfume, and (b) from about 50% to about 99.5% by weight, based on the weight of the particles of a matrix comprising at least one water dispersible amine of the formula $$R—N\ R^1R^2$$

where R is an alkyl or alkenyl group having from 8 to 22 carbon atoms, $R^1$ is hydrogen or an alkyl or alkenyl group having 1 to 4 carbon atoms and $R^2$ is hydrogen or an alkyl, alkenyl or amino-alkyl group having from 1 to 22 carbon atoms, the matrix containing no added cationic material; and (ii) a second phase constituting from about 0.5% to about 80% by weight of the composition and comprising a fabric conditioning agent.

2. A method according to claim 1, characterised in that the fabric conditioning composition is supported on a flexible substrate.

3. A method according to claim 1, characterised in that the fabric conditioning composition is in particulate form and is sprinkled over the fabrics in the dryer.

4. A method according to claim 1, characterised in that the fabric conditioning composition is in liquid form and is sprayed onto the inside surfaces of the dryer and/or onto the fabrics prior to operation of the dryer.

5. A method according to claim 1, characterised in that the fabric conditioning composition is in the form of a paste or cream which is applied to a portion of the fabrics prior to operation of the dryer.

6. A product for depositing perfume on fabrics in a rotary hot air dryer, comprising a fabric conditioning composition supported on a flexible substrate, characterised in that said fabric conditioning composition comprises (i) a first phase constituting from about 0.5% to about 50% by weight of the composition and consisting of particles having an average size of from about 0.1 micron to about 200 microns, the particles comprising an intimate mixture of (a) from about 0.5% to about 50% by weight, based on the weight of the particles, of a perfume, and (b) from about 50% to about 99.5% by weight, based on the weight of the particles of a matrix comprising at least one water dispersible amine of the formula $$R—N\ R^1R^2$$

where R is an alkyl or alkenyl group having from 8 to 22 carbon atoms, $R^1$ is hydrogen or an alkyl or alkenyl group having 1 to 4 carbon atoms and $R^2$ is hydrogen or an alkyl, alkenyl or amino-alkyl group having from 1 to 22 carbon atoms, the matrix containing no added cationic material; and (ii) a second phase constituting from about 0.5% to about 80% by weight of the composition and comprising a fabric conditioning agent.

* * * * *